(12) United States Patent
McMinn et al.

(10) Patent No.: US 9,066,730 B2
(45) Date of Patent: Jun. 30, 2015

(54) MEDICAL DEVICE

(75) Inventors: Derek McMinn, Birmingham (GB);
Charles Desoutter, Hertfordshire (GB);
Matthew Gooch, Hertfordshire (GB)

(73) Assignee: Smith & Nephew plc, London (GB)

( * ) Notice: Subject to any disclaimer, the term of this patent is extended or adjusted under 35 U.S.C. 154(b) by 2015 days.

(21) Appl. No.: 11/816,777

(22) PCT Filed: Feb. 21, 2006

(86) PCT No.: PCT/GB2006/000605
§ 371 (c)(1),
(2), (4) Date: Apr. 8, 2008

(87) PCT Pub. No.: WO2006/087584
PCT Pub. Date: Aug. 24, 2006

(65) Prior Publication Data
US 2008/0287952 A1 Nov. 20, 2008

(30) Foreign Application Priority Data
Feb. 21, 2005 (GB) .................................. 0503529.0

(51) Int. Cl.
*A61B 17/16* (2006.01)
*A61B 17/00* (2006.01)

(52) U.S. Cl.
CPC .......... *A61B 17/1624* (2013.01); *A61B 17/1666* (2013.01); *A61B 2017/00738* (2013.01); *A61B 17/1631* (2013.01)
USPC ......................................................... 606/80

(58) Field of Classification Search
USPC .............................................. 606/80–85, 86 R
See application file for complete search history.

(56) References Cited

U.S. PATENT DOCUMENTS

| 5,236,433 | A | * | 8/1993 | Salyer | 606/91 |
|---|---|---|---|---|---|
| 5,916,231 | A | * | 6/1999 | Bays | 606/180 |
| 6,312,438 | B1 | * | 11/2001 | Adams | 606/159 |
| 6,451,058 | B2 | * | 9/2002 | Tuke et al. | 623/22.21 |
| 6,733,218 | B2 | * | 5/2004 | Del Rio et al. | 409/231 |
| 7,326,215 | B2 | * | 2/2008 | Myers et al. | 606/80 |
| 7,637,909 | B2 | * | 12/2009 | Lechot et al. | 606/80 |
| 7,819,875 | B2 | * | 10/2010 | Chana | 606/81 |

(Continued)

FOREIGN PATENT DOCUMENTS

| WO | WO 03/065906 A2 | 8/2003 |
|---|---|---|
| WO | WO 03/092513 A1 | 11/2003 |

OTHER PUBLICATIONS

International Preliminary Report on Patentability, International Application No. PCT/GB2006/000605, 7 pages.

(Continued)

*Primary Examiner* — Christopher Beccia
(74) *Attorney, Agent, or Firm* — Krieg DeVault LLP (57) ABSTRACT

An attachment for a surgical instrument including a drive input hub for connection to a power source; a drive output hub for connection to a surgical instrument; and a body connecting the drive input hub to the drive output hub, the body including a mechanism for transferring drive from the input hub to the output hub, and wherein the body, the drive input hub and the drive output hub are at least in part not coaxial. A method for surgically preparing a bone using the attachment is also provided.

29 Claims, 6 Drawing Sheets

(56) References Cited

U.S. PATENT DOCUMENTS

| | | | |
|---|---|---|---|
| 2003/0050645 A1* | 3/2003 | Parker et al. | 606/99 |
| 2004/0087958 A1* | 5/2004 | Myers et al. | 606/80 |
| 2005/0216022 A1* | 9/2005 | Lechot et al. | 606/81 |
| 2005/0277970 A1* | 12/2005 | Norman et al. | 606/180 |
| 2006/0276797 A1* | 12/2006 | Botimer | 606/81 |

OTHER PUBLICATIONS

Canadian Office Action dated Apr. 18, 2012; Candian Application No. 2,601,920; 3 pages.

Japanese Office Action: Japanese Patent Office; dated Jun. 10, 2014; Japanese Application No. 2013-142763; 7 pages.

* cited by examiner

| ITEM NO. | DESCRIPTION |
| --- | --- |
| 1 | HOUSING, OUTPUT |
| 2 | HOUSING |
| 3 | HOUSING |
| 4 | HOUSING, INPUT |
| 5 | ATTACHMENT CASE |
| 6 | PLANET CARRIER |
| 7 | INTERNAL GEAR |
| 8 | BEARING |
| 9 | PIN |
| 10 | CAGED NEEDLE ASSEMBLY |
| 11 | PLANET WHEEL |
| 12 | BEARING |
| 13 | WASHER |
| 14 | ATTACHMENT PINION |
| 15 | BEARING |
| 16 | CIRCLIP |
| 17 | SPIGOT |
| 18 | CIRCLIP |
| 19 | CLAMP SCREW |
| 20 | PIN |
| 21 | O RING |
| 22 | END CAP |
| 23 | SHAFT, REAMER END |
| 24 | REAMER SHELL |
| 25 | SCREW – SPECIAL |
| 26 | BEARING |
| 27 | BEARING |
| 28 | BEARING |
| 29 | BEVEL GEAR |
| 30 | SPACER |
| 31 | SPACER, LONG |
| 32 | BEARING SPACER, SHORT |
| 33 | TURNBUCKLE |
| 34 | SHAFT |
| 35 | SHAFT, SHORT |
| 36 | BEARING LINER |
| 37 | CIRCLIP |
| 38 | CIRCLIP |
| 39 | CIRCLIP |
| 40 | CIRCLIP |
| 41 | KEY |
| 42 | O RING |
| 43 | RETAINING RING |
| 44 | BALL |
| 45 | PIN |
| 46 | BALL GUIDE PIN |
| 47 | RETAINING RING |
| 48 | GUIDE PIN |
| 49 | SPACER |
| 50 | O RING |
| 51 | WIRE RING |
| 52 | SPACER |

| ITEM NO. | DESCRIPTION |
|---|---|
| 1 | HOUSING, OUTPUT |
| 2 | HOUSING |
| 3 | HOUSING |
| 4 | HOUSING, INPUT |
| 5 | END CAP |
| 6 | SHAFT, REAMER END |
| 7 | SCREW – SPECIAL |
| 8 | BEARING |
| 9 | BEARING |
| 10 | BEARING |
| 11 | BEARING |
| 12 | BEARING |
| 13 | BEARING |
| 14 | BEVEL GEAR |
| 15 | SPACER |
| 16 | SPACER, LONG |
| 17 | BEARING SPACER, SHORT |
| 18 | TURNBUCKLE |
| 19 | SHAFT |
| 20 | SHAFT, SHORT |
| 21 | BEARING LINER |
| 22 | CIRCLIP |
| 23 | CIRCLIP |
| 24 | CIRCLIP |
| 25 | CIRCLIP |
| 26 | CIRCLIP |
| 27 | CIRCLIP |
| 28 | KEY |
| 29 | O RING |
| 30 | O RING |
| 31 | O RING |
| 32 | RETAINING RING |
| 33 | BALL |
| 34 | PIN |
| 35 | PIN |
| 36 | PIN |
| 37 | BALL GUIDE PIN |
| 38 | RELEASING COLLAR |
| 39 | GUIDE PIN |
| 40 | SPACER |
| 41 | SPACER |
| 42 | ATTACHMENT CASE |
| 43 | PLANET CARRIER |
| 44 | INTERNAL GEAR |
| 45 | CAGED NEEDLE ASSEMBLY |
| 46 | PLANET WHEEL |
| 47 | WASHER |
| 48 | ATTACHMENT PINION |
| 49 | SPIGOT |
| 50 | CLAMP SCREW |
| 51 | SPRING |
| 52 | SHIM |
| 53 | SHIM |
| 54 | E CLIP |
| 55 | REAMER SHELL |

MEDICAL DEVICE

The present invention relates to an attachment for a surgical instrument, particularly a cutting device such as a reamer.

In-line acetabular reamer attachments are known in which the attachment consists of a straight tubular body with a drive input at one end and a drive output at the other end. The drive input and output are coupled by a drive train housed in the attachment body which transfers drive from the input to the output. In use, a suitable power tool is connected to the drive input and an acetabular reamer cutting shell is attached to the drive output.

In surgical operations it is common for the Surgeon to need to operate around/behind obscuring body parts. For example, in the case of the acetabular re-surfacing procedure, the femoral head obscures the cutting site. Conventional in-line acetabular reamer attachments are therefore not effective, and the Surgeon has to make a large incision in order to insert the in-line acetabular reamer attachment and perform the operation. Such action is clearly disadvantageous for the Surgeon and the patient.

It is therefore desirable to provide a device that enables the Surgeon to manoeuvre around obscuring body parts and perform operations behind such obscuring body parts. It is also desirable to provide a minimally invasive device that requires the Surgeon to make a minimal incision in order to use the device.

The present invention provides a device that enables a Surgeon to manoeuvre around obscuring body parts and perform an operation behind such obscuring body parts.

According to a first aspect of the present invention, there is provided an attachment for a surgical instrument, comprising:
   a drive input hub for connecting, in use, to a power source;
   a drive output hub for connecting, in use, to a surgical instrument; and
   a body connecting the drive input hub to the drive output hub, the body comprising means for transferring drive from the input hub to the output hub,
   wherein the body, the drive input hub and the drive output hub are at least in part not coaxial.

In this application, the feature that the body, the drive input hub and the drive output hub are at least in part not coaxial means that these three components are not all in linear alignment. Thus, attachments according to the present invention are not so-called in-line attachments. However, this does not mean that some or even parts of the three components cannot be in linear alignment. For example, the drive input hub and the drive output hub may be in linear alignment with each other, but not with the body or part of the body. The body or part of the body may be in linear alignment with the drive input hub, but not with the drive output hub, for example. The body or part of the body may be in linear alignment with the drive output hub, but not with the drive input hub, for example.

Preferably, the body comprises a curved portion.

Preferably, the body comprises a plurality of sections that are angularly disposed with respect to each other.

According to a preferred embodiment of the present invention, the attachment for a surgical instrument comprises:
   a drive input hub for connecting, in use, to a power source;
   a drive output hub for connecting, in use, to a surgical instrument; and
   a body connecting the drive input hub to the drive output hub, the body comprising means for transferring drive from the input hub to the output hub,
   wherein the body comprises a plurality of sections that are angularly disposed with respect to each other.

The shape/configuration of the attachment has the advantage that a Surgeon can manoeuvre it around/past body parts that are obscuring the target of the surgery. The surgical instrument can be positioned behind the obscuring body part.

The shape/configuration of the attachment has the advantage that prior to insertion of the attachment the Surgeon can make a minimal incision.

According to an embodiment of the present invention, the attachment body comprises:
   a first section to which the drive input hub is attached;
   a second section to which the drive output hub is attached; and
   a third section connecting the first and second sections, wherein the longitudinal axes of the first and second sections are disposed at an angle with respect to the longitudinal axis of the third section.

The angle between the longitudinal axes of the first and third sections may be the same as the angle between the longitudinal axes of the second and third sections.

The angle between the longitudinal axes of the first and third sections and/or the angle between the longitudinal axes of the second and third sections may be between plus or minus 20 and 80 degrees, or between plus or minus 20 and 75 degrees, or between plus or minus 25 and 70 degrees, or between plus or minus 30 and 65 degrees, or between plus or minus 40 and 65 degrees, or between plus or minus 45 and 65 degrees, or between plus or minus 50 and 65 degrees.

Preferably, the angle between the longitudinal axes of the first and third sections is about plus or minus 60 degrees. Preferably, the angle between the longitudinal axes of the second and third sections is about plus or minus 60 degrees.

The means for transferring drive from the input hub to the output hub may comprise a series of universal joints.

The means for transferring drive from the input hub to the output hub may comprise one or more flexible shafts.

According to a preferred embodiment of the present invention, the means for transferring drive from the input hub to the output hub comprises a series of drive shafts and bevel gears, the drive shafts being angularly disposed with respect to each other.

The angle between adjacent drive shafts may be between plus or minus: 20 and 80 degrees; 20 and 75 degrees; 25 and 70 degrees; 30 and 65 degrees; 40 and 65 degrees; 45 and 65 degrees; or 50 and 65 degrees.

Preferably, the angle between adjacent drive shafts is about plus or minus 60 degrees.

According to a preferred embodiment of the present invention, the attachment comprises three drive shafts respectively disposed in the first, second and third sections of the body, the drive shafts being coupled by bevel gears.

The overall length of the attachment measured from the end of the drive input hub to the end of the drive output hub may be between 150 and 450 mm, preferably between 200 and 400 mm, more preferably between 250 and 350 mm. Lengths in the range 300 to 320 mm are particularly preferred.

The length of the first section may be between 30 and 90 mm, preferably between 45 and 75 mm, more preferably between 50 and 70 mm.

The length of the second section may be between 30 and 90 mm, preferably between 45 and 75 mm, more preferably between 50 and 70 mm.

The length of the third section may be between 100 and 300 mm, preferably between 100 and 200 mm, more preferably between 120 and 160 mm. Lengths in the range 130 to 150 mm are particularly preferred.

Preferably, the body is tubular. The body may have a diameter between 15 and 45 mm, preferably between 20 and 40 mm, more preferably between 25 and 35 mm.

The attachment may be made of any suitable material. For example, the attachment may be made of one or more metals or one or more alloys, or a combination of metal(s) and alloy(s).

The components of the attachment may be made of the same or different materials.

The body may be made of aluminium, aluminium alloy, stainless steel or titanium, for example. Preferably, the body is made of a light material. Preferably, the body is made of aluminium or aluminium alloy.

Preferably, the drive shafts and bevel gears are made of steel, more preferably stainless steel.

The surgical instrument may be a cutting device. The cutting device may be a reamer cutting shell, for example an acetabular reamer cutting shell.

Preferably, the drive input hub and the drive output hub are coaxial. That is, the input and output hubs are preferably in linear alignment.

Preferably, the power source is a rotary drive source.

The power source may be an electric power tool, for example an electric drill.

The power source may be a pneumatic power tool.

According to a second aspect of the present invention, there is provided a reamer for surgically preparing a bone, comprising an attachment according to the first aspect of the present invention in combination with a reamer cutting shell.

Preferably, the reamer of the second aspect further comprises a rotary drive source.

According to a third aspect of the present invention, there is provided a method for surgically preparing a bone, comprising the steps of:

providing an attachment for a surgical instrument according to the first aspect of the present invention;

providing a surgical instrument for machining a surface of the bone;

providing a power source;

connecting the surgical instrument and the power source to the attachment;

inserting the surgical instrument and attachment through an incision in the patient;

positioning the surgical instrument against a bone surface while positioning the attachment around intervening anatomy; and driving the surgical instrument to machine the bone surface.

According to a fourth aspect of the present invention, there is provided a method for surgically preparing a bone, comprising the steps of:

providing an attachment for a surgical instrument comprising a drive input hub connectable to a power source, a drive output hub connectable to a surgical instrument, and a body connecting the drive input hub to the drive output hub, the body comprising means for transferring drive from the input hub to the output hub, wherein the body, the drive input hub and the drive output hub are at least in part not coaxial;

providing a surgical instrument for machining a surface of the bone;

connecting the surgical instrument to the drive output hub;

providing a power source;

connecting the power source to the drive input hub;

inserting the surgical instrument and attachment through an incision in the patient;

positioning the surgical instrument against a bone surface while positioning the attachment around intervening anatomy; and driving the surgical instrument to machine the bone surface.

The surgical instrument may be an acetabular reamer, and the bone surface may be an acetabulum.

Reference will now be made, by way of example, to the accompanying drawings in which.

An attachment for a reamer cutting shell in accordance with the present invention is illustrated in FIGS. 1-11. As shown in FIGS. 1, 2, 5 and 6, the reamer comprises six main assemblies, namely a universal conical connection spigot (part of the drive input hub), a reduction gearbox (part of the drive input hub), a body comprising a drive train, a reamer drive assembly (part of the drive output hub), a reamer shell retention mechanism (part of the drive output hub) and an acetabular reamer cutting shell, which is releasably attached to the drive output hub. The component parts of the reamers shown in FIGS. 1 and 2 and FIGS. 5 and 6 are listed in FIGS. 4 and 9, respectively.

Referring to FIGS. 1 to 4, in use a powered handpiece drives an epicyclic gearbox (6-12) inside the reamer attachment, thereby reducing the speed and increasing the torque. Drive is transferred along the reamer attachment's unique shape to the reamer shell cutter (24) drive hub via a series of drive shafts (34,35) and bevel gears (29). The use of bevel gears (29) allows the drive to be taken through a much more acute angle in comparison with universal joints or flexible shafts. Likewise bevel gears (29) withstand far higher running or slam torques.

Figures 1, 2, 3:
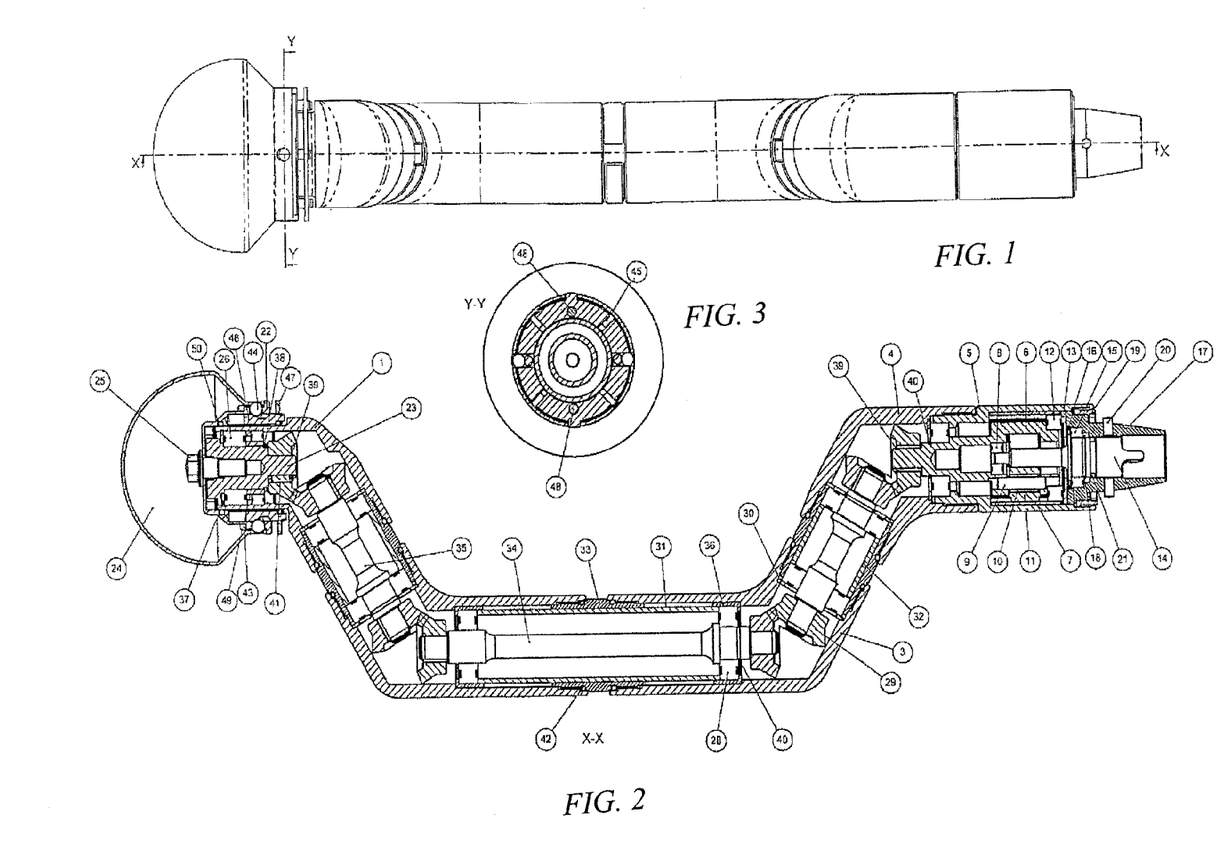
FIG. 1 is a plan view of an attachment according to the present invention.
FIG. 2 is a cross-sectional view of the attachment shown in FIG. 1, taken along line X-X of FIG. 1.
FIG. 3 is a cross-sectional view of the attachment shown in FIG. 1, taken along line Y-Y of FIG. 1.
Figure 4:
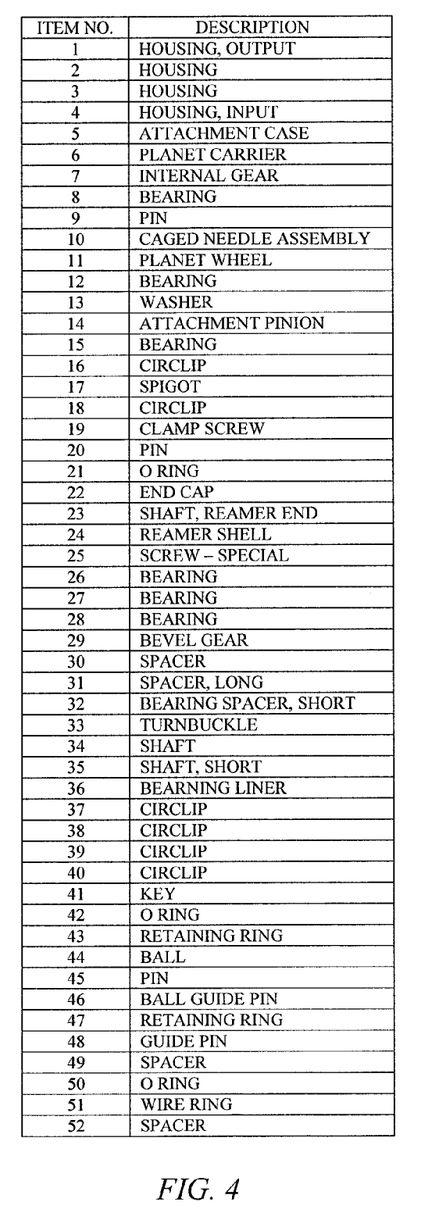
FIG. 4 is a key to FIGS. 1-3.
Figure 5:
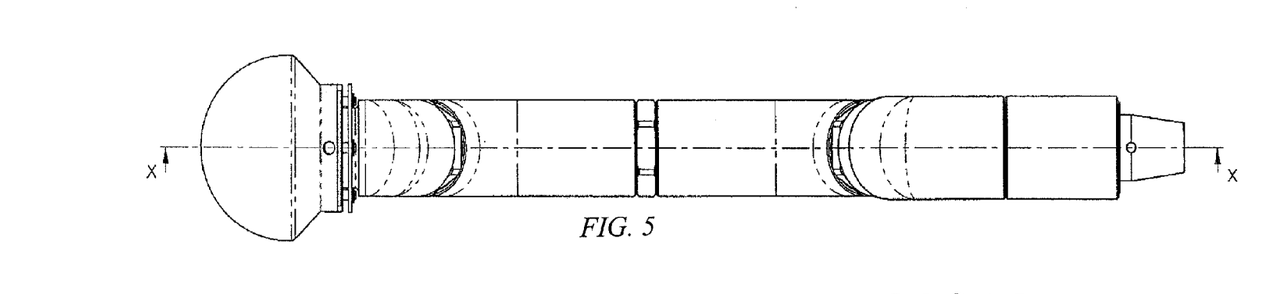
FIG. 5 is a plan view of an attachment according to the present invention.

As shown in FIG. 2, the design of the final drive output hub incorporates the bearing/shaft assembly within the internal space envelope of the rear portion of the acetabular shell (24). This has the effect of reducing, to an absolute minimum, the distance between the distal end of the acetabular reamer cutting shell (24) and the rear of the angle head (1).

The reamer attachment shown in FIGS. 1 and 2 has a unique acetabular reamer cutting shell (24) locking system, enabling the reamer shell cutter to be locked securely onto the drive hub (22) whilst the reamer is in use. The cutting shell is locked axially in place by two balls (44) which are radially held out into two corresponding holes within the driving collar on the reamer shell (24). The balls are held in the outward position by the plain portion on the two notched pins (46) which are secured onto the releasing collar (47). The whole releasing collar and notched pin assembly is spring loaded away from the distal end of the reamer shell (24). Depressing the collar towards the distal end of the reamer shell allows the balls to enter the notched portion of the two pins, this in turn enables the reamer shell to be withdrawn over the balls and the drive hub (22) assembly. The drive hub incorporates two drive dogs, which locate into two corresponding slots on the rear portion of the reamer shell mounting collar, this provides the drive between the drive hub and the shell.

To give the unique shape of the attachment, typical angles of the drive shaft and bevel gears are between 20 and 80 degrees plus or minus from the axis but also between 20 and 75 degrees, 25 and 70 degrees, 30 and 65 degrees, 40 and 65 degrees, 45 and 65 degrees and 50 and 65 degrees plus or minus from the axis of the shaft. Aptly an angle of 60 degrees, or about 60 degrees plus or minus from the axis of the shaft may be used to give the unique shape of the attachment.

An attachment for a reamer cutting shell in accordance with the present invention will now be described in more detail with reference to FIGS. 6 to 11.

Figure 6:
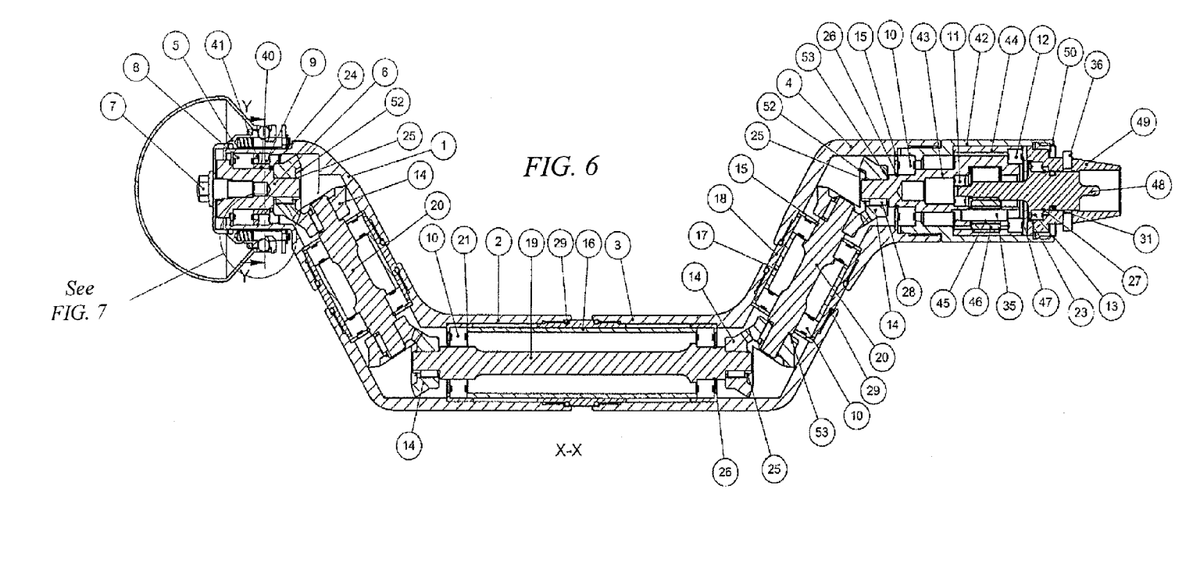
FIG. 6 is a cross-sectional view of the attachment shown in FIG. 5, taken along line X-X of FIG. 5.

In use, the universal conical connection spigot assembly (49) is inserted into a surgical motor handpiece (not shown) with the output drive from the handpiece connecting to the input shaft attachment pinion (48) by means of a tang shaped drive end. The powered handpiece output speed is normally around 1000-1200 rpm.

A reamer attachment having a universal conical connection spigot assembly (49) is a preferred embodiment of the present invention. Such reamer attachments are designed to be used with the De Soutter Medical MDX electric (battery) and MPX pneumatic surgical instrument systems. However, alternative configurations are possible. For example, the conical connection spigot arrangement can be replaced with a conventional Hudson, Zimmer or other industry standard chucking system. Such configurations necessitate the use of a separate geared reamer attachment with its associated drawbacks.

The reduction gearbox assembly reduces the output speed of the powered handpiece down to the required acetabular reaming speed, typically between 200 and 300 rpm. This speed reduction is achieved by a single stage planetary gearbox system. The attachment pinion (48) is supported on two bearings (11,13), the gear form on the pinion engaging on the planet wheels (46). The attachment pinion is sealed against water and steam ingress by a seal (31) assembled to the attachment pinion (48). The planet carrier (43) is supported on two bearings (12,10) and is driven by the resultant rotary motion created between the attachment pinion (48), the planet wheels (46) and the internal gear (44). A bevel gear (14) is mounted onto a shouldered spigot diameter formed on the distal end of the planet carrier (43). A key (28) transmits the drive between the planet carrier (43) and the bevel gear (14).

The body (1-4) takes the drive train through a deformed U-shaped, or top hat shaped, series of bends around the patient's femoral head. This particular design comprises four separate bends with the output drive from the reamer preferably ending up being in line with the original axis of the handpiece output drive. The series of bends in the drive train is achieved by configuring four sets of bevel gears (14) arranged in such a manner that their axis of rotation form a typical angle to one another of 120 degrees. The bevel gear sets are connected by three shafts (19,20) that are supported on a number of bearings (10) mounted into the angled housings (2,3,4) of the body. The housings are connected by three turnbuckles (18) and supporting spacers (16,17) which control the correct dimensional relationships between the assembled components so ensuring the bevel gears (14) are correctly meshed. The transmission is therefore taken through four bends of 120 degrees each. The offset distance between the input axis from the handpiece to the secondary parallel transmission axis is typically around 50 mm. The distance between the two bends, which defines the length of secondary parallel transmission axis, typically measures 140 mm.

The output shaft (6) is driven from the final set of bevel gears (14) which is supported on two bearings (8,9), which in turn are retained within the output housing (1). The drive between the output shaft and the end cap (5) is accomplished by dog drive machined onto the internal face of the end cap and the front of the shaft. The two items are secured together with a screw (7). The whole front-end reamer hub assembly is sealed against the ingress of liquid and steam by a seal (30) located between the internal annulus of the end cap (5) and the outside diameter of the output housing (1). A feature of the output hub assembly is that the output shaft (6) and supporting bearing assembly (8,9) is so arranged that it partially protrudes into, and is thereby incorporated within, the internal space envelope of the rear portion of the acetabular reamer shell (55). This has the effect of reducing, to the absolute minimum, the distance between the distal end of the acetabular reamer shell (55) and the back face of the output housing (1).

The end cap (5) acts as the location spigot for the rear annulus of the reamer shell (55), whilst containing a quick release locking mechanism to retain the reamer shell. As shown in more detail in FIG. 7, the locking mechanism comprises a series of interacting notched pins (37) and balls (33) which secure the reamer shell (55) to the end cap (5). The notched pins are pushed rearwards by springs (51) which are retained within the end cap (5) assembly. The notched pins are secured into the releasing collar (38) and are stopped from rotation by having flats machined onto their ends, the flatted notched pin ends mating with corresponding D holes formed into the releasing collar (38). With the releasing collar (38) and notched pins (37) taking up their normal position the balls (33) are held radially out against the retaining ring (32). The holes in the retaining ring (32) are sized such that they keep the balls (33) captive whilst at the same time they allow the balls (33) to partially protrude beyond the retaining ring (32) diameter when acting on the full diameter of the notched pins (37). The reamer shell (55) is released from the end cap assembly by pushing the spring-loaded releasing collar (38) towards the distal end of the device, this action allows the notched portion of the notched pins (37) to line up with the balls (33) thereby allowing the balls to retract inwardly. The balls retracting below the outside diameter of the end cap assembly allows the reamer shell (55) to be slid off distally. The drive between the reamer shell (55) and the end cap (5) is achieved by the inclusion of two lugs that are machined onto the rear portion of the end cap (5). These lugs mate with two corresponding notches that are formed into the rear location diameter on the reamer shell (55).

Figure 7:
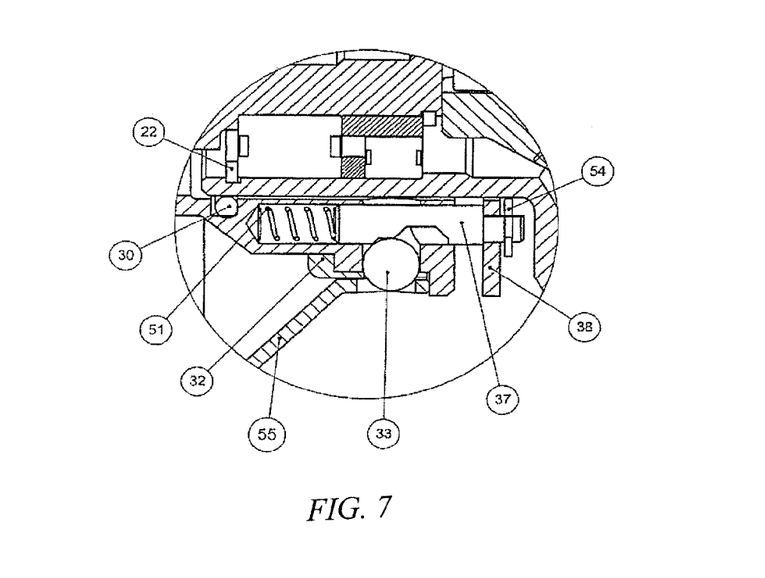
FIG. 7 is an enlarged cross-sectional view of part of the attachment shown in FIG. 6.
Figure 8:
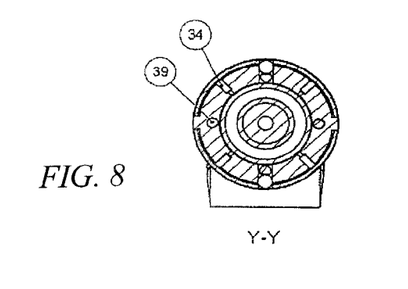
FIG. 8 is a cross-sectional view of the attachment shown in FIG. 6, taken along line Y-Y of FIG. 6.
Figure 9:
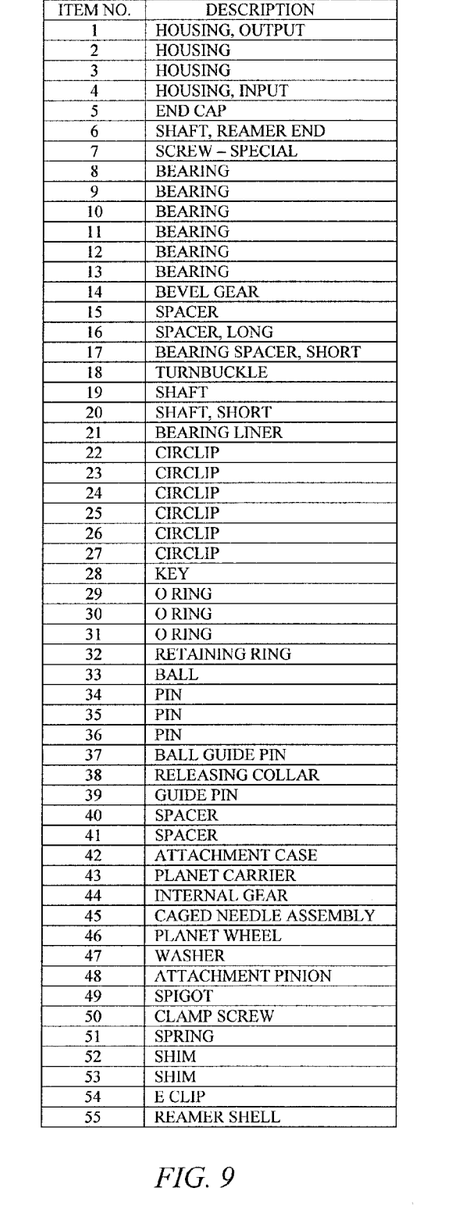
FIG. 9 is a key to FIGS. 5-8.
Figure 10:
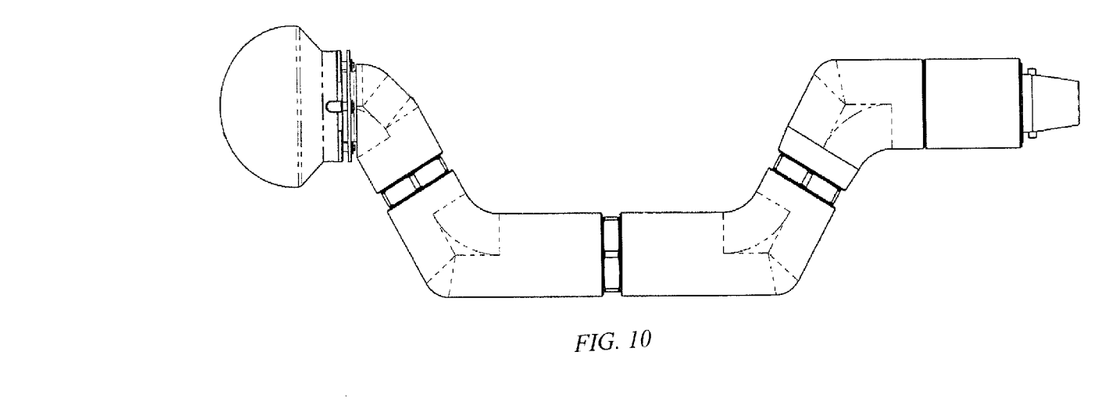
FIG. 10 is a side view of an attachment according to the present invention in which a reamer cutting shell is attached.
Figure 11:
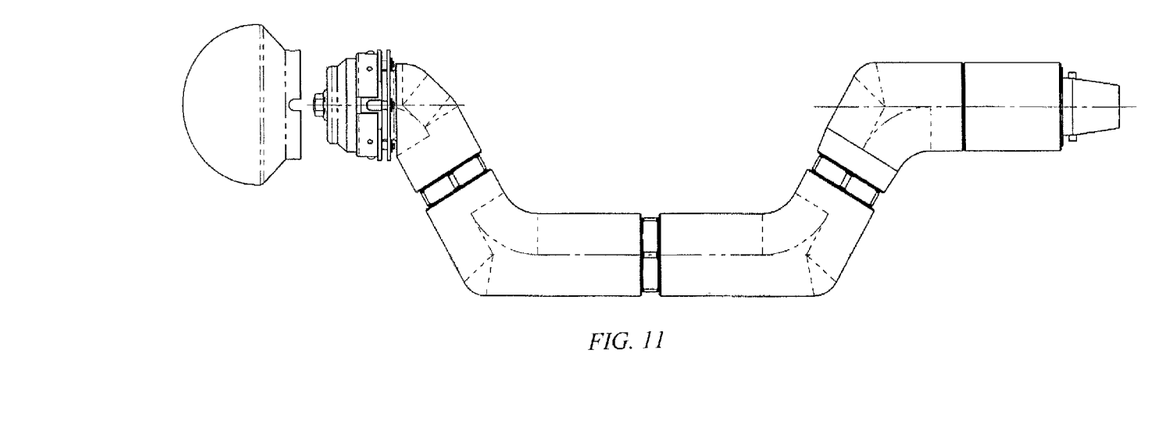
FIG. 11 is a side view of an attachment according to the present invention in which a reamer cutting shell is detached.

The acetabular reamer shell (55) is constructed in a similar fashion to those commonly used for acetabulum reaming procedures. However, reamer shells used with the attachment of the present invention are configured to contain two drive notches formed into the rear location diameter.

An attachment according to the present invention is a dedicated device that improves the surgeon's ability to perform various acetabular reaming procedures where access to the surgical site is limited. Typically access is restricted in hip re-surfacing procedures and least invasive total hip replacement (THR) hip surgery. The uniquely shaped reamer attachment allows the surgeon to make a much smaller incision than would otherwise be required when using a conventional in-line acetabular reamer shaft assembly.

Devices according to the present invention enable the thrust line to be kept perpendicular to the cutting site when performing least invasive surgical techniques. A problem associated with the hip re-surfacing procedure is that the femoral head obscures the cutting site. Additionally the distance between the femoral head and the acetabulum is severely restricted when the surgeon inserts the reamer head/shell assembly into the surgical site. The attachment according to the present invention overcomes these problems by enabling the drive train from the powered handpiece to curve around the obscuring femoral head so that cutting behind the obscuring femoral head can occur.

Reamer attachments according to the present invention optimise the available space by utilising a very compact drive train mechanism, which has a very acute angle of approach and which incorporates both the final angled drive hub assembly and the reamer shell retention/releasing mechanism. The use of bevel gears allows the drive to be taken through a much more acute angle in comparison with alternative transmission systems such as universal joints or flexible shafts. Bevel gears can withstand far higher running or slam/stall torques which are often encountered in acetabular reaming procedures.

Attachments according to the present invention incorporate a reduction gearbox, typically having a gearing reduction of 5:1, which eliminates the necessity of utilising a separate geared reamer attachment connected to the motor handpiece. In this single attachment configuration, the weight, length and general bulk of the powered handpiece/attachment combination is minimised. As there is only one coupling point between the handpiece and the reamer attachment the complete system becomes far more robust and rigid than would normally be the case with a separate secondary attachment containing the reduction gearbox. A further advantage of this configuration is that the outer casing of the reamer attachment is both rotationally and axially secured into the handpiece by the universal conical locking mechanism. As a result, the reaming reaction torque is transmitted back into the pistol grip shaped handpiece, which in turn eliminates the necessity of incorporating a side handle onto the reamer attachment.

Although the attachment of the present invention has been described in relation to a reamer, it can be used as a tool driver for other surgical instruments (tools).

The invention claimed is:

1. An attachment for a surgical instrument, comprising:
a drive input hub for connection to a power source;
a drive output hub for connection to a surgical instrument; and
a body connecting the drive input hub to the drive output hub, the body comprising a drive train for transferring drive from the input hub to the output hub, wherein the body, the drive input hub and the drive output hub are at least in part not coaxial wherein the drive train comprises a plurality of drive shafts rotationally coupled to one another by a series of bevel gears, and wherein longitudinal axes of adjacent ones of the drive shafts are angularly disposed with respect to one another to define an acute angle therebetween of at least 45degrees but less than 90degrees.

2. An attachment according to claim 1, wherein the body comprises a curved portion.

3. An attachment according to claim 1, wherein the body comprises a plurality of sections that are angularly disposed with respect to each other.

4. An attachment according to any of claims 1, wherein the body comprises:
a first section to which the drive input hub is attached;
a second section to which the drive output hub is attached; and
a third section connecting the first and second sections, wherein the longitudinal axes of the first and second sections are disposed at an angle with respect to the longitudinal axis of the third section.

5. An attachment according to claim 4, wherein the angle between the longitudinal axes of the first and third sections is the same as the angle between the longitudinal axes of the second and third sections.

6. An attachment according to claim 1, wherein the body is made of aluminum.

7. An attachment according to claim 1, wherein the surgical instrument is a cutting device.

8. An attachment according to claim 7, wherein the cutting device is a reamer cutting shell.

9. An attachment according to any preceding claim 1, wherein the drive input hub and the drive output hub are coaxial.

10. An attachment according to claim 1, wherein the power source is a rotary drive source.

11. An attachment according to claim 1, wherein the drive train includes at least three of the drive shafts, and wherein adjacent pairs of the drive shafts are rationally coupled to one another by corresponding pairs of the bevel gears.

12. An attachment according to claim 1, wherein the drive train includes at least three of the drive shafts, and wherein adjacent pairs of the drive shafts are angularly disposed with respect to one another.

13. An attachment according to claim 1, wherein the drive input hub includes an input shaft rotationally coupled to a first of the drive shafts, and wherein the drive output hub includes an output shaft rationally coupled to a second of the drive shafts.

14. An attachment according to claim 13, wherein the input shaft is rationally coupled to the first drive shaft by a first pair of intermeshing bevel gears, and wherein the output shaft is rationally coupled to the second drive shaft by a second pair of intermeshing bevel gears.

15. An attachment according to claim 14, wherein the first drive shaft is rationally coupled to a third of the drive shafts by a third pair of intermeshing bevel gears, and wherein the third drive shaft is rotationally coupled to the second drive shaft by a forth pair of intermeshing bevel gears.

16. An attachment for a surgical instrument, comprising:
a drive input hub for connection to a power source;
a drive output hub for connection to a surgical instrument; and
a body connecting the drive input hub to the drive output hub, the body comprising a drive train for transferring drive from the input hub to the output hub, wherein the body, the drive input hub and the drive output hub are at least in part not coaxial, wherein the drive train comprises a plurality of drive shafts rationally coupled to one another by a series of bevel gears, and wherein longitudinal axes of adjacent ones of the drive shafts are angularly disposed with respect to one another to define an acute angle therebetween of at least 45 degrees but less than 90 degrees; and
wherein the drive input hub includes an input shaft and a reduction gear assembly coupled between the input shaft and an adjacent one of the drive shafts to reduce the rotational speed of the drive train relative to the input shaft.

17. An attachment according to claim 16, wherein the reduction gear assembly comprises a reduction gearbox.

18. An attachment according to claim 17, wherein the reduction gearbox comprises a single-stage planetary gearbox.

19. An attachment according to claim 16, further comprising a rotary motor attached to the input shaft and a cutting device attached to an output shaft of the drive output hub; and
wherein the reduction gear assembly reduces an output rotational speed of the cutting device relative to an input rotational speed of rotary motor.

20. An attachment for a surgical instrument, comprising:
a drive input hub for connection to a power source;
a drive output hub for connection to a surgical instrument;
a body connecting the drive input hub to the drive output hub, the body comprising a drive train for transferring drive from the input hub to the output hub, wherein the body, the drive input hub and the drive output hub are at least in part not coaxial, wherein the drive train comprises a plurality of drive shafts rotationally coupled to one another by a series of bevel gears, and wherein longitudinal axes of adjacent ones of the drive shafts are angularly disposed with respect to one another to define an acute angle therebetween of at least 45 degrees but less than 90 degrees; and
a rotary motor attached to the input shaft; and
wherein the drive input hub includes an input shaft and a reduction gear assembly coupled between the input shaft and an adjacent one of the drive shafts to reduce the rotational speed of the drive train relative to the input shaft; and
wherein the reduction gear assembly is incorporated into the body and is coupled to the input shaft and the adjacent drive shaft to reduce the rotational speed of the adjacent drive shaft relative to the rotational speed of the rotary motor.

21. An attachment according to claim 16, wherein the input shaft, the reduction gear assembly and the adjacent drive shaft are axially aligned with one another along a longitudinal axis of the adjacent drive shaft.

22. An attachment according to claim 1, wherein the acute angle is less than 80 degrees.

23. An attachment according to claim 1, wherein the acute angle is between 45 degrees and 65 degrees.

24. An attachment according to claim 23, wherein the acute angle is about 60 degrees.

25. An attachment according to claim 1, further comprising a reamer cutting shell connected to the drive output hub;
wherein the reamer cutting shell defines an internal space envelope; and
wherein the drive output hub includes an output shaft and a shaft supporting bearing positioned within the internal space envelope of the reamer cutting shell.

26. An attachment according to claim 25, wherein the reamer cutting shell is locked to the drive output hub by a plurality of balls radially positioned in a corresponding number of recesses.

27. An attachment according to claim 26, wherein the recesses comprises notches defined in a corresponding number of pins.

28. An attachment according to claim 27, wherein the pins are spring loaded in an axial direction.

29. An attachment according to claim 1, wherein a first of the adjacent ones of the drive shafts has a length extending along a first longitudinal axis, wherein a second of the adjacent ones of the drive shafts has a length extending along a second longitudinal axis, and wherein the first and second longitudinal axes are angularly disposed with respect to one another to define the acute angle therebetween of at least 45 degrees but less than 90 degrees.

* * * * *